US012575951B2

(12) United States Patent
Asgeirsson et al.

(10) Patent No.: US 12,575,951 B2
(45) Date of Patent: Mar. 17, 2026

(54) LINER HAVING DIFFERENT REGIONS OF ELONGATION

(71) Applicant: Ossur Iceland ehf, Reykjavik (IS)

(72) Inventors: Sigurdur Asgeirsson, Reykjavik (IS); Larus Sigfusson, Reykjavik (IS); Linda Ros Birgisdottir, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 933 days.

(21) Appl. No.: 17/825,528

(22) Filed: May 26, 2022

(65) Prior Publication Data

US 2022/0280317 A1 Sep. 8, 2022

Related U.S. Application Data

(63) Continuation of application No. 16/223,479, filed on Dec. 18, 2018, now Pat. No. 11,369,496.

(60) Provisional application No. 62/608,451, filed on Dec. 20, 2017.

(51) Int. Cl.
*A61F 2/78* (2006.01)
*A61F 2/50* (2006.01)
*A61F 2/80* (2006.01)

(52) U.S. Cl.
CPC .............. *A61F 2/7812* (2013.01); *A61F 2/78* (2013.01); *A61F 2002/5007* (2013.01); *A61F 2002/7818* (2013.01); *A61F 2002/785* (2013.01); *A61F 2/80* (2013.01)

(58) Field of Classification Search
CPC .. A61F 2/7812; A61F 2/78; A61F 2002/7818; A61F 2002/785
See application file for complete search history.

(56) References Cited

U.S. PATENT DOCUMENTS

| | | | |
|---|---|---|---|
| 2,325,656 A | 7/1943 | Brophy | |
| 3,099,266 A | 7/1963 | Spitzer | |
| 3,600,717 A | 8/1971 | McKeehan | |
| 4,023,384 A | 5/1977 | Conti et al. | |
| 4,237,707 A | 12/1980 | Safrit et al. | |
| 4,319,413 A | 3/1982 | Mattil | |
| 4,474,573 A | 10/1984 | Detty | |
| 4,492,227 A | 1/1985 | Senn et al. | |
| 4,554,749 A | 11/1985 | Ostrander | |
| 4,632,106 A | 12/1986 | Gamm | |
| 4,635,626 A | 1/1987 | Lerman | |
| 4,885,828 A | 12/1989 | Kozlowski | |

(Continued)

FOREIGN PATENT DOCUMENTS

| | | |
|---|---|---|
| WO | 0051537 A1 | 9/2000 |
| WO | 0167842 A1 | 9/2001 |
| WO | 2009003486 A1 | 1/2009 |

OTHER PUBLICATIONS

International Search Report from Corresponding PCT Application No. PCT/US2018/0066155, Mar. 29, 2019.

*Primary Examiner* — Bruce E Snow
(74) *Attorney, Agent, or Firm* — Workman Nydegger

(57) ABSTRACT

A prosthetic liner includes a textile cover having at least first and second regions having different elongation from one another. The first region is in a prestretched configuration in at least one orientation relative to an axis of the prosthetic liner and locked in the prestretched configuration according to a layer of elastomeric material located along a surface of the textile cover.

14 Claims, 4 Drawing Sheets

(56) References Cited

U.S. PATENT DOCUMENTS

| | | | |
|---|---|---|---|
| 4,908,037 | A | 3/1990 | Ross |
| 4,923,474 | A | 5/1990 | Klasson et al. |
| 5,115,650 | A | 5/1992 | Patrick et al. |
| 5,244,716 | A | 9/1993 | Thornton et al. |
| 5,263,923 | A | 11/1993 | Fujimoto |
| 5,367,708 | A | 11/1994 | Fujimoto |
| 5,407,421 | A | 4/1995 | Goldsmith |
| 5,474,524 | A | 12/1995 | Carey |
| 5,593,454 | A | 1/1997 | Helmy |
| 5,640,714 | A | 6/1997 | Tanaka |
| 5,830,237 | A | 11/1998 | Kania |
| 5,885,674 | A | 3/1999 | Maemoto et al. |
| 5,888,216 | A | 3/1999 | Haberman |
| 6,059,834 | A | 5/2000 | Springs |
| 6,076,284 | A | 6/2000 | Terlizzi |
| 6,136,039 | A | 10/2000 | Kristinsson et al. |
| 6,149,690 | A | 11/2000 | Belzidsky |
| 6,171,431 | B1 | 1/2001 | Gallagher, Jr. et al. |
| 6,282,729 | B1 | 9/2001 | Oikawa et al. |
| 6,406,499 | B1 | 6/2002 | Kania |
| 6,454,812 | B1 | 9/2002 | Laghi |
| 6,485,776 | B2 | 11/2002 | Janusson et al. |
| 6,572,574 | B2 | 6/2003 | Gardon-Mollard |
| 6,592,539 | B1 | 7/2003 | Einarsson et al. |
| 6,626,952 | B2 | 9/2003 | Janusson et al. |
| 6,706,364 | B2 | 3/2004 | Janusson et al. |
| 6,726,641 | B2 | 4/2004 | Chiang et al. |
| 6,852,269 | B2 | 2/2005 | Eberle et al. |
| 6,964,688 | B1 | 11/2005 | Kania |
| 7,001,563 | B2 | 2/2006 | Janusson et al. |
| 7,025,738 | B2 | 4/2006 | Hall |
| 7,025,793 | B2 | 4/2006 | Egilsson |
| 7,090,651 | B2 | 8/2006 | Chiang et al. |
| 7,118,602 | B2 | 10/2006 | Bjarnason |
| 7,169,189 | B2 | 1/2007 | Bjarnason et al. |
| 7,291,182 | B1 | 11/2007 | Kania |
| 7,297,128 | B2 | 11/2007 | Binder et al. |
| 7,351,264 | B2 | 4/2008 | Wilson |
| 7,713,222 | B2 | 5/2010 | Evans et al. |
| 7,909,884 | B2 | 3/2011 | Egilsson et al. |
| 8,034,120 | B2 | 10/2011 | Egilsson et al. |
| 8,070,828 | B2 | 12/2011 | Shannon |
| 8,123,818 | B2 | 2/2012 | Bjarnason et al. |
| 9,770,891 | B2 | 9/2017 | Bjarnason et al. |
| 9,974,668 | B2 | 5/2018 | Halldorsson et al. |
| 10,376,391 | B2 * | 8/2019 | Halldorsson .......... A61F 2/7812 |
| 11,369,469 | B2 * | 6/2022 | Gross ................... A61F 2/2418 |
| 2001/0039159 | A1 | 11/2001 | Janusson et al. |
| 2002/0002405 | A1 | 1/2002 | Janusson et al. |
| 2002/0165619 | A1 | 11/2002 | Hellberg |
| 2002/0183859 | A1 | 12/2002 | Houser |
| 2003/0181989 | A1 | 9/2003 | Eberle et al. |
| 2005/0101693 | A1 | 5/2005 | Arbogast et al. |
| 2005/0115112 | A1 | 6/2005 | Bonfanti |
| 2005/0155137 | A1 | 7/2005 | Berger |
| 2005/0240283 | A1 | 10/2005 | Kania |
| 2006/0165939 | A1 | 7/2006 | Hottner |
| 2007/0027556 | A1 | 2/2007 | Wilson |
| 2007/0033711 | A1 | 2/2007 | Achtelstetter |
| 2007/0043450 | A1 | 2/2007 | Pickering et al. |
| 2007/0061017 | A1 | 3/2007 | Wilson |
| 2007/0123998 | A1 | 5/2007 | Egilsson et al. |
| 2008/0188949 | A1 | 8/2008 | MacKenzie |
| 2008/0221705 | A1 | 9/2008 | Scussel |
| 2008/0221706 | A1 | 9/2008 | Scussel et al. |
| 2009/0036999 | A1 | 2/2009 | Egilsson et al. |
| 2009/0132056 | A1 | 5/2009 | Kania |
| 2010/0274363 | A1 | 10/2010 | Laghi et al. |
| 2011/0098827 | A1 | 4/2011 | Laghi et al. |
| 2011/0118854 | A1 | 5/2011 | Halldorsson |
| 2011/0208321 | A1 | 8/2011 | Doddroe et al. |
| 2011/0270414 | A1 | 11/2011 | Laghi et al. |
| 2013/0331952 | A1 | 12/2013 | Halldorsson et al. |
| 2016/0338858 | A1 | 11/2016 | Hurley et al. |
| 2019/0269530 | A1 | 9/2019 | Mosler et al. |

* cited by examiner

LINER HAVING DIFFERENT REGIONS OF ELONGATION

FIELD OF THE DISCLOSURE

The disclosure relates to a prosthetic liner arranged for suspension in a prosthetic socket, and more particularly to a liner having different regions of elongation.

BACKGROUND

Prosthetic liners are arranged for fitting over a residual limb and serve as an interface between the residual limb and a prosthetic socket. As no residual limb is the same, there are challenges for effectively and intimately fitting a liner during use. These challenges relate to comfort, fit and function, and include durability, moisture-control, residual limb volume fluctuations, temperature, and migration or pistoning of the liner during use.

A prosthetic liner typically has a tubular and/or conical shape, with a first or proximal end being open ended, and a second or distal end being closed-ended. These liners are typically made from a layer of air impermeable elastomeric material and may include a reinforcement layer intermediate the inner and outer surfaces of the body portion of the liner or externally thereof to provide resistance against axial elongation of the elastomer constituting the liner body. Such reinforcement typically does not restrict radial distension or stretching of the liner body. A textile cover may be on the outer surface of the liner and adjacent or layered relative to the layer of elastomeric material.

Prosthetic liners formed from elastomeric materials have been described in prior patents, such as, for example, U.S. Pat. No. 4,923,474 issued May 8, 1990; U.S. Pat. No. 5,507,834 granted Apr. 16, 1996; U.S. Pat. No. 5,376,129 granted Dec. 27, 1994; and U.S. Pat. No. 6,485,776, granted Nov. 26, 2002; each of these patents are incorporated herein by their entirety. Elastomeric liners are used to cushion a post-operative stump or residual limb regarding a prosthesis installed over the residual limb and coupled to the socket by a locking element as described in U.S. Pat. No. 5,376,129. The suspension of the prosthesis occurs due to the suction of the liner against the residual limb.

It is highly desirable in such liners that they conform closely with the residual limb, accommodate all surface contours and sub-surface bone elements of the residual limb and provide a comfortable cushion between the residual limb and the hard socket of the prosthesis to be fitted over the residual limb.

Special elastomer materials have been formulated as suitable substances for liners. Such elastomer materials having suitable hardness (or softness), elongation, tensile and other properties (sterilizability, non-porous, easily cleanable, etc.) have been used successfully for suspension liners.

The liner disclosed in U.S. Pat. No. 4,923,474 includes an elasticity controlling matrix material at the distal end of a textile cover about which the elastomeric material is coated so the textile cover does not impede elasticity of the elastomer radially within the normal range of radial distension of the liner in normal use. The elasticity controlling matrix material renders the liner substantially inelastic axially during use to minimize the "pumping" effect that can occur with a fully resilient liner at the distal end of a residual limb that may not be fully healed or sealed as discussed in this patent.

As explained in U.S. Pat. No. 6,485,776, an elasticity-controlling matrix material is typically integrated within the thickness of the elastomeric material, whereas the textile cover has a substantially uniform elasticity. The elasticity-controlling matrix provides anisotropy of elasticity between radial and axial directions, with the liner remaining radially elastic but substantially inelastic axially at the distal end area of the liner.

Unwanted translation, rotation and pistoning movement may occur between a residual limb, liner and socket, even if there is a close fit. Such movement may occur during gait, and a distal pin on the liner engaging the socket may cause tension being applied distally to the residual limb, which results in a "milking" phenomenon or the pistoning movement with the tension offset by compression varying during gait. This variable tension or rotation of the residual limb relative to the socket during may lead to edema, discoloration, pain, volume loss and discomfort due to compression about the residual limb varying likewise.

It is highly desirable to increase the comfort of such liners to enhance their ability to conform to irregularities on the residual limb, to accommodate a wider variety of residual limbs with fewer sizes of liners; and to provide the amputee with a total feeling of comfort at the residual limb interface with the prosthesis, all while maintaining strength and durability of the liner. It is likewise desirable to offer such liner in a manner that limits manufacturing steps and simplifies the basic construction of the liner.

SUMMARY

According to embodiments of the disclosure, a prosthetic liner has at least two regions of different axial elongation relative to an axis of the liner. Preferably, a distal portion of the liner is configured to have less axial elongation relative to an adjacent region of liner relative to the axis of the liner. The textile cover of the liner itself may control the elasticity of the liner due to prestretching of sections of the textile cover prior to providing an elastomeric layer thereon. The prestretching of regions of the textile cover imparts a structural feature because elasticity is inhibited in at least one direction relative to an axis of the liner. The prestretching may occur in an axial direction, which is locked in place by the elastomeric material, while stretching or elongation of the axially prestretched region in a radial direction is generally the same as in regions of the textile cover that did not undergo prestretching.

This arrangement is advantageous in that the textile cover can be modified prior to securing the elastomeric material to the textile cover, such that it offers the manufacturer greater flexibility in adapting the textile cover to uniform or non-uniform axial elongation within the distal portion and/or other regions of the liner. The adaptation of the axial elongation permits better adaptability to a residual limb (particularly in view of the phenomena of pumping, milking, and other problems) and enables the manufacturer to offer many textile covers having varying axial elongation depending on anatomy of the residual limb, and type and level of activity.

According to an embodiment of the disclosure, a prosthetic liner comprises a textile cover having at least first and second regions each with a different elongation relative to one another. The first region is in a prestretched configuration in at least one orientation relative to an axis of the liner and is locked in the prestretched configuration by and/or according to a layer of elastomeric material cured and located along a surface of the textile cover. The second region may be generally unstretched relative to the first region and with the layer of elastomeric material secured thereon. The textile cover may form an exterior of the prosthetic liner as in prior art liners, and the layer of elastomeric material may be located along an entirety of the textile cover extending continuously between the first and second regions.

The first region may be prestretched in an axial direction relative to the axis such that elongation in axial direction is inhibited relative to axial elongation of the second region. This configuration inhibits milking of the liner when in use and may aid likewise in mitigation of rotation of the liner at the distal end, particularly when a distal pin extends from the liner and locks with a prosthetic socket. The first region may be prestretched in other directions, such as radially, relative to the axis of the liner.

A defined demarcation may be located between the first and second regions to clearly distinguish the prestretched configuration from an adjacent region of the textile cover that may not be prestretched or is altered relative to the prestretched configuration. In one variation, the demarcation is transverse relative to the axis of the liner. The demarcation may vary or extend in different directions relative to the axis of the liner.

The demarcation may be shifted and defined according to requirements of a user. The demarcation may be arranged so the first region increases from anterior to posterior sides of the liner with the demarcation rising proximally toward a proximal end of the liner relative to a distal end of the liner relative to the axis. Such an arrangement may be defined according to gait and the areas of the liner that may undergo more milking and require more rotation control.

In a variation, the first region may comprise at least one elongate region rising proximally toward a proximal end of the liner relative to a distal end of the liner and the axis. In another variation, the first region may have a gradient in which elongation varies and may extend axially relative to the axis.

The textile cover may be arranged such that in an unstretched configuration, the first and second regions have a same elongation and consist of a same textile cover continuously extending along a combined length of the first and second regions along the axis in both circumferential and axial directions of the liner about an outer periphery of the liner. The definition of a same elongation comprises at least a same elongation in radial and axial directions.

The liner may have a conventional shape of a liner because it has a closed-ended distal end and an open-ended proximal end. According to a preferred embodiment, the first region is located at the closed-ended distal end of the liner to mitigate milking and rotation when in use. The second region may be located proximally relative to the first region. The second region may be substantially longer than the first region relative to the axis of the liner to allow for sufficient elasticity and elongation in axial and radial directions to assure a proper fit and comfort to the user. The first region may be confined solely or mostly in or to the distal portion of the liner, or at least originating in the distal portion of the liner, and thereby coinciding with a distal end cap and corresponding distal pin (if provided).

These and other features of the present disclosure will become better understood regarding the following description, appended claims, and accompanying drawings.

Figures 1, 2:
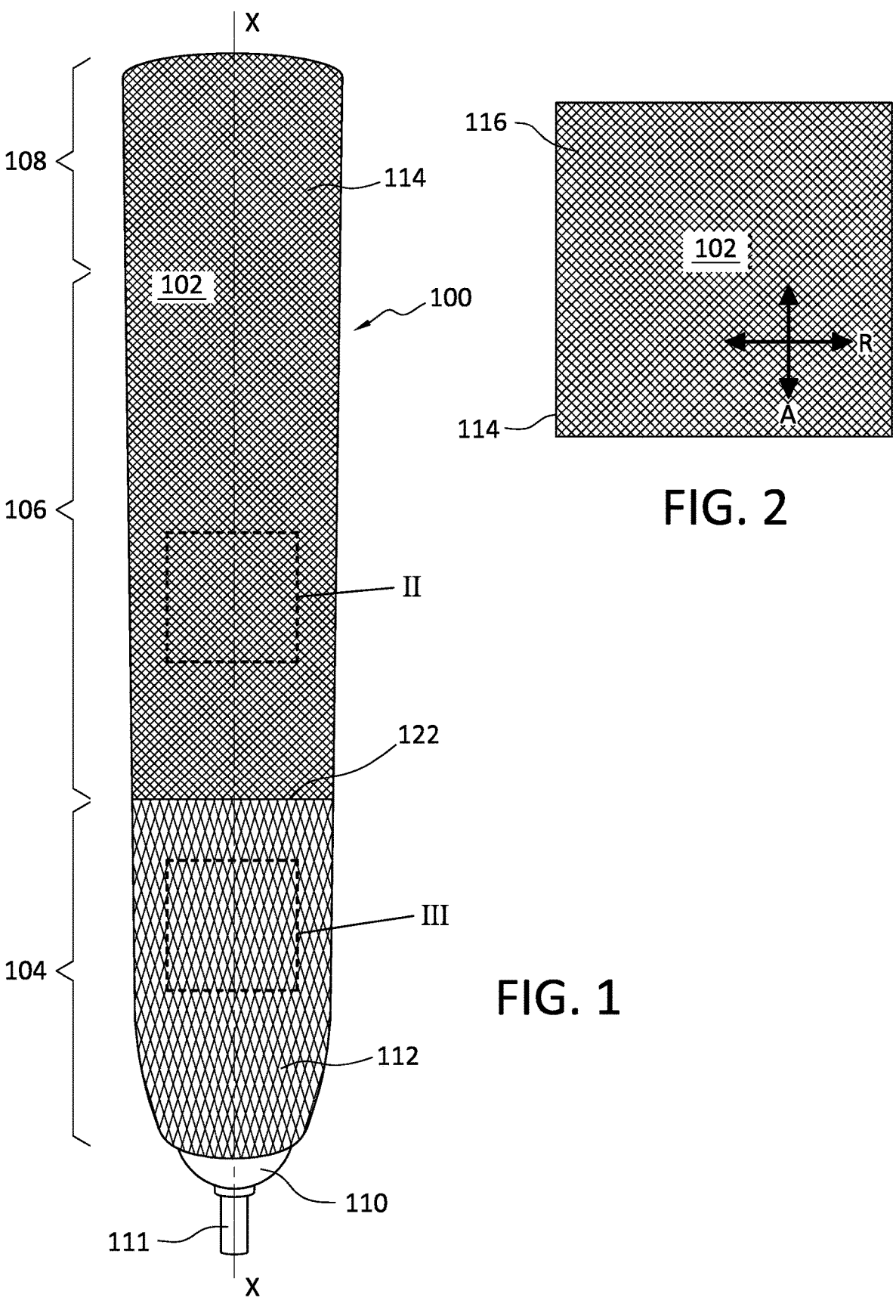
FIG. 1 is an elevational view showing an exemplary embodiment of a liner having different regions of axial elongation along axis X-X.
FIG. 2 is a detail view taken from FIG. 1 of an intermediate portion of a textile cover.

The drawing figures are not necessarily drawn to scale, but instead are drawn to provide a better understanding of the components, and are not intended to be limiting in scope, but rather to provide exemplary illustrations. Each of the liners depicted in the figures has a similar axis to axis X-X in FIG. 1.

DETAILED DESCRIPTION OF VARIOUS EMBODIMENTS

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the embodiments disclosed, but on the contrary, the intention covers all modifications, alternative constructions, combinations, and equivalents falling within the spirit and scope of the disclosure.

It will be understood that, unless a term is defined in this disclosure to possess a described meaning, there is no intent to limit the meaning of such term, either expressly or indirectly, beyond its plain or ordinary meaning. As each of the embodiments herein include an elastomeric material, such elastomeric material may be one known in the art of liners, including thermoplastic (e.g., polyurethane) or thermoset (e.g., silicone), and combinations thereof, and may likewise include additives as known in the art of liners.

FIG. 1 illustrates an embodiment of a prosthetic liner 100 having a textile cover 102 with at least one layer of elastomeric material (not shown) along an inner surface of the textile cover 102, as taught in the prior art. The liner 100 may have a closed-ended distal portion 104, an intermediate portion 106, and an open-ended proximal portion 108. The portions 104, 106, 108 are relative to a central, longitudinal axis X-X. A distal end cap 110 may be secured to the distal portion 104 depending on the liner 100 and its intended use. The distal end cap 110 may have no elasticity and is substantially more rigid than the textile cover 102. The distal end cap 110 is secured to the liner 100 and may carry a distal pin 111 for securing to a prosthetic socket, as is well known in the art of prosthetic devices.

According to disclosed embodiments, the textile cover 102 preferably has different regions of axial elongation and possesses a uniform elasticity when not subject to pretensioning. The distal portion 104 defines an axially stretched configuration 112, and the intermediate and proximal portions 106, 108 comprise an axially non-stretched configuration 114 thereby having a different axial elongation than the first textile axially stretched configuration 112. In at least the embodiment of FIG. 1, the stretched and non-stretched configurations 112, 114 are preferably defined by the same textile cover 102 and demarcated by line 122.

By the same textile, at least according to the embodiment of FIG. 1, this should mean that a continuous textile is employed between the distal and proximal portions 104, 108 and across the intermediate portion 106. Prior to forming the liner 100, the textile cover 102 preferably has the same properties, such as axial and radial elongation, continuously from end to end, e.g. from proximal to distal ends. Such an arrangement eliminates a necessity to secure different textile segments to one another to form the textile cover 102 or knit regions in the textile cover 102 having different properties. The benefits of such an arrangement should be clear and include at least minimization in cost and simplicity in manufacturing.

Regarding the expression "stretched" or "preconfigured for inhibiting elongation" in either axial or radial directions, it should mean that prior processing of the textile cover requires pretensioning a region of the textile cover prior to securing an elastomer layer therein or thereto. The stretched region or section is preconfigured for inhibiting elongation in contrast with a "non-stretched" region that does not undergo prior processing at least regarding tensioning of the textile cover. While "stretched" and "non-stretched" are defined in the context of manufacture, these properties result in structural qualities that lead to functional qualities of the textile cover, and hence the liner.

FIG. 1 depicts a demarcation or line 122 that discretely separates the stretched and non-stretched configurations 112, 114. Such discrete separation facilitates isolation of the elongation or non-elongation of the textile cover 102 and enables particularly arranged regions to correspond to individual regions of a user's residual limb. The discrete separation of the stretched and non-stretched configurations 112, 114 also guides functionality of the liner 100 regarding a socket in which it is inserted. The separation of the stretched and non-stretched configurations 112, 114 can also prevent detrimental forces by controlling an amount of axial elongation to prevent "milking" and rotation of the residual limb relative to the socket during gait, yet offer sufficient radial elongation to permit the liner to conform to a variety of residual limb shapes.

Figures 4A, 4B, 4C, 5A, 5B, 5C:
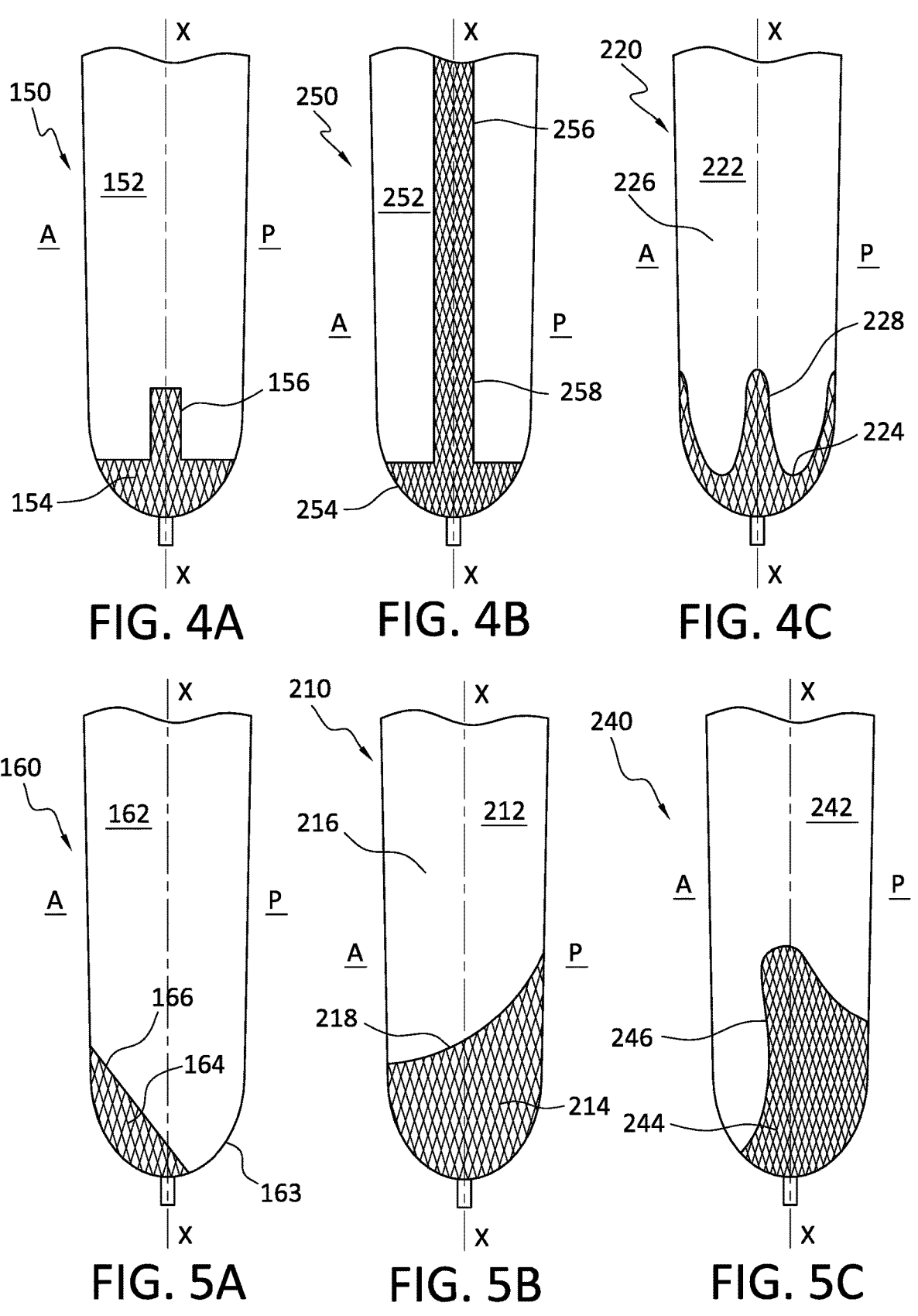
FIG. 4A is an elevational view of a variation of the liner of FIG. 1 having at least one elongate region of preconfigured axial elongation.
FIG. 4B is an elevational view showing another variation of the liner of FIG. 1 having at least one elongate region of preconfigured axial elongation.
FIG. 4C is an elevational view showing another variation of the liner of FIG. 1 having at least one elongate region of preconfigured axial elongation.
FIG. 5A is an elevational view showing a variation of the liner of FIG. 1 having a variable demarcation between first and second regions.
FIG. 5B is an elevational view showing a variation of the liner of FIG. 1 having another variable demarcation between first and second regions.
FIG. 5C is an elevational view showing a variation of the liner of FIG. 1 having another variable demarcation between first and second regions.

While FIG. 1 shows the demarcation 122 as being transverse to the axis X-X, such arrangement is merely exemplary, and such demarcation 122 may be modified according to many configurations relative to a residual limb, as explained regarding FIGS. 5A-5C. The demarcation 122 may be circumferential or may be arranged in discrete regions about a circumference of the liner 100. The demarcation 122 may be variable in that not only is the demarcation 122 about discrete regions of a circumference of the liner 100, but it may alter axially according to the location of a discrete region relative to its intended placement about the limb of a user.

FIG. 1 shows the demarcation 122, while separating the stretched and non-stretched configurations 112, 114, as being continuous in that there is no seam, but rather the same textile cover 102 extends into both stretched and non-stretched configurations 112, 114 albeit with discrete pretensioning. The liner 100 may be modified so the demarcation 122 separates at least two textile panels or covers each having predetermined properties, such as elongation, and the demarcation 122 may comprise a structural feature, such as a seam or union between such at least two textile panels.

Although the demarcation 122 is provided, according to an embodiment, the stretched and non-stretched configurations 112, 114 maintain a same, continuously knitted structure across their entirety, with their only difference resulting from the distal portion 104 being pretensioned against the elastomeric material which maintains the pretensioned configuration of the distal portion 104 as the layer of elastomeric material is formed and/or cured thereon, thereby defining the stretched configuration 112. The intermediate and proximal portions 106, 108 may have a greater axial elongation since they are not pretensioned to the same level as the distal portion 104, the material of the textile cover 102 thereby having discrete properties in different portions.

As shown in FIG. 1, the axially stretched configuration defines a first region 112 which is in a distal portion 104 of the liner 100, and the axially non-stretched configuration 114 defines a second region 114, which is located proximally relative to the first region 112 from the demarcation 122 of the first and second regions 112, 114. The second region 114 extends longer along the axis X-X than the first region 112 such that first region 112 is preferably confined to the distal portion 104 of the liner 100. The first region 112 may be configured to extend at least less than the length of the intermediate portion 108 and may extend a length substantially equal to at least half of the intermediate portion 108. The length of the distal portion 104 relative to the intermediate portion 106 may vary according to a length of a residual limb and may be dictated as such. It may be desirable to limit the length of the distal portion 104, and hence the first region 112 relative to the intermediate and proximal portions 106, 108 to assure elongation or elasticity of the liner 100 about the residual limb aside from or external to the distal portion 104 for proper fit and retention on a residual limb.

Specifically, the stretched configuration 112 is formed by a pretensioned portion of the textile cover 102, whereby prior to being pretensioned in the distal portion 104, the textile cover 102 maintains a uniform elasticity and axial elongation. By stretching the distal portion 104 during manufacturing, such as prior to adherence of an elastomer to the textile cover 102 or maintaining a stretched configuration 112 during adherence of an elastomer to the textile cover 102, the textile cover 102 may be locked in the stretched configuration 112 at least by a layer of the elastomeric material which cures, according to known principles discussed in the aforementioned prior art, and thereby secures or impregnates to a surface of the textile cover 102. The cured elastomeric material locks the textile cover 102 in the stretched configuration 112, with the result that the distal portion 104 can have a low axial elongation.

It will be understood that when the liner 100 is donned, the non-stretched configuration 114 may undergo stretching to conform to the residual limb anatomy, however the non-stretched configuration 114 is the state as predetermined prior to donning of the liner 100. The stretched configuration 112 is predetermined and possesses its configuration when the liner 100 is not donned, although it may undergo some additional stretching when the liner 100 is donned, but not to the same degree that the non-stretched configuration 114 will undergo. The stretched configuration 112 is preferably stretched in an axial direction, and is anisotropic in that it may be stretched only or primarily in the axial direction along the axis X-X. The stretched configuration 112 may be additionally and preferably stretchable in a radial direction relative to the axis X-X, and substantially more than it is stretchable in the axial direction.

As an alternative, there may be controlled prestretching of the distal portion 104 or other prestretched region relative to the non-stretched configuration 114. However, such prestretching may not be to the extent such that the stretched configuration is in an extreme, such that there is no axial elongation of the distal portion 104. Rather, the prestretching is done to create relative elongation among different predetermined regions. Such prestretching is not limited to the distal portion 104 but may be performed at any predetermined region of the liner 100 and may be configured according to regions of the residual limb. The liner 100 is not limited to adaptation of only two regions, but rather multiple regions may be provided with different prestretching relative to one another, and such prestretching may be done in variable directions relative to the axis X-X, such as axial and/or radial prestretching or combinations thereof.

If the elastomer is a thermoplastic, the thermoplastic may adapt over time due to repeated donning to a specific shape of a user's residual limb. The prestretched regions may be matched to intended regions of a user's residual limb that will undergo shaping by the adaptation of the thermoplastic to a user's limb.

FIG. 1 generally shows the textile cover 102 in the distal portion 104 being generally circumferential because the stretched configuration 112 is consistent about a circumference of the liner 100 relative to the axis X-X of the liner 100.

FIG. 2 shows a portion II of the textile cover 102 in a relaxed or non-stretched state or configuration 114, which results in the textile cover 102 having a tighter knitted structure 116 in both axial A and radial R directions, as the textile cover 102 is elastic in both radial R and axial A directions.

Figure 3A:
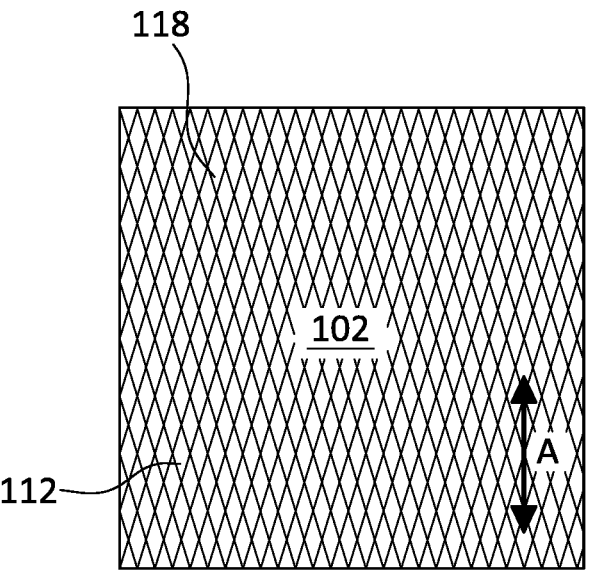
FIG. 3A is a detail view taken from FIG. 1 of a distal portion of the same textile cover in FIGS. 1 and 2 and showing pre-tensioning of the textile cover toward axial elongation.

FIG. 3A shows a portion III of the textile cover 102 in the stretched state or configuration 112, such that the textile cover 102 is stretched in the axial direction A leaving a more open knitted structure 118 in at least the axial direction A. The more open knitted structure may inhibit substantial or more axial elongation. The stretched state or configuration may have or allow radial elongation R and/or permit being prestretched or tensioned in the axial direction A.

Figure 3B:
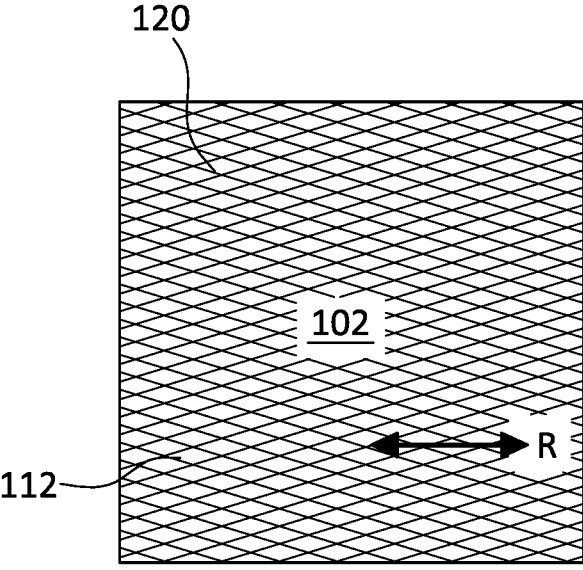
FIG. 3B is a detail view of a variation of FIG. 3A showing pre-tensioning of the textile cover toward radial elongation.

FIG. 3B is a variation of FIG. 3A showing how the textile cover 102 may be prestretched in a radial direction R and having an open knitted structure 120 so that axial elongation A is allowed and/or without allowing substantial or more radial elongation. Alternatively, the textile cover 102 may be adapted as a combination of both FIGS. 3A and 3B whereby there is prestretching in both the axial and radial directions A, R relative to the natural or inherent stretchability of the textile cover 102, as depicted in FIG. 2.

As discussed within the context of FIG. 1 that the textile cover 102 is prestretched prior to adherence of an elastomeric material thereon, an additional material or matrix may be provided instead of stretching such textile cover 102. The matrix may be prestretched similarly to the textile cover 102 or may have inherent properties that inhibit elongation. The matrix may be added to the textile cover 102, either exterior or interior of the textile cover 102, or provided in combination with the elastomeric material, either within a thickness of the elastomeric material or along an inner or exterior surface of the elastomeric material. The matrix may be a textile, or may be another elastomer, resin or other suitable material that will inhibit elongation in a predetermined orientation. This variation applies to any of the embodiments described herein.

FIG. 4A depicts a variation of the liner 100 of FIG. 1, in that the liner 150 of FIG. 4A has a variably stretched textile cover 152, comprising at least one finger or elongate region 156 extending generally along an anterior-posterior plane dividing anterior and posterior sides A, P of the liner 150 along the axis X-X. The liner 150 may comprise at least two fingers 156 on opposed sides of the liner 150. The at least one elongate region 156 and a region 154 distal of the at least one elongate region 156 may likewise be in a stretched configuration, whereas areas outside of the at least one elongate region 156 and the distal portion 154 may be configured in a non-stretched or variable elongation configuration relative to the textile cover 152.

FIG. 4B exemplifies a variation of a liner 250 from the liner 100 of FIG. 4A wherein at least one elongate region 256 extends generally along an anterior-posterior plane dividing anterior and posterior sides A, P of the liner 250 from the distal end 254 to a proximal end. The at least one elongate region 256 preferably may have, but is not limited to having, a limited axial elongation relative to the textile cover 252. The at least one elongate region 256 may have a different axial elongation along its length, whereby the distal end 254 and a distal portion 258 of the at least one elongate region 256 may have a greater inhibition to stretching than near a proximal end of the liner 250 to prevent distal milking of the liner 250 when in use. The limited axial stretching properties of the at least one elongate region 256 may be attained through prestretching as described in relations to previous embodiments, and it will be understood that the at least one elongate region 256 may alternatively or concurrently be prestretched to limit radial elongation.

FIG. 4C depicts a variation of a liner 220 from the liner 100 of FIG. 1 wherein a plurality of fingers 228 extend from a distal end 224 of the liner 100. The plurality of fingers 228 and the distal end 224 have reduced elongation or axial stretching relative to a region 226 of the textile cover 222 outside of the distal end 224. The plurality of fingers 228 reach into areas of the region 226 and are configured in shape to reduce milking and rotation of the liner 220 when in use. The fingers 228 are shaped and distributed about the distal end 224 of the liner 220 to taper toward the proximal end and distributed distal forces on the liner 220.

FIG. 5A illustrates a liner 160 as a variation of the liner 100 of FIG. 1, with a distal end 164 that changes variably according to a profile 166 relative to the anterior and posterior sides A, P of the liner 160 (relative to a user's residual limb) and the axis X-X. In this embodiment, the profile 166 exemplifies how the distal end 164 can have an axial elongation that is different, such as having less axial elongation, than a region 163 of the textile cover 162 outside of the distal end 164.

FIG. 5B depicts a liner 210 as another variation of the liner 100 of FIG. 1, wherein the distal end 214 has a different elongation from a region 216 of the textile cover 212 outside of the distal end 214. The distal end 214 has a variably shaped profile 218 relative to the axis X-X, much as in FIG.

5A, with a greater proportion of the textile cover 212 being formed as a pre-stretched region and/or having different elongation properties.

FIG. 5C illustrates a liner 240 as another variation of the liner 100 of FIG. 1. As in FIGS. 5A and 5B, the distal end 244 has a variable profile 246 relative to the axis X-X of the liner 240 and extends variably generally along the axis X-X. The distal end 244 has a variable elongation relative to the textile cover 242.

Figures 6, 7:
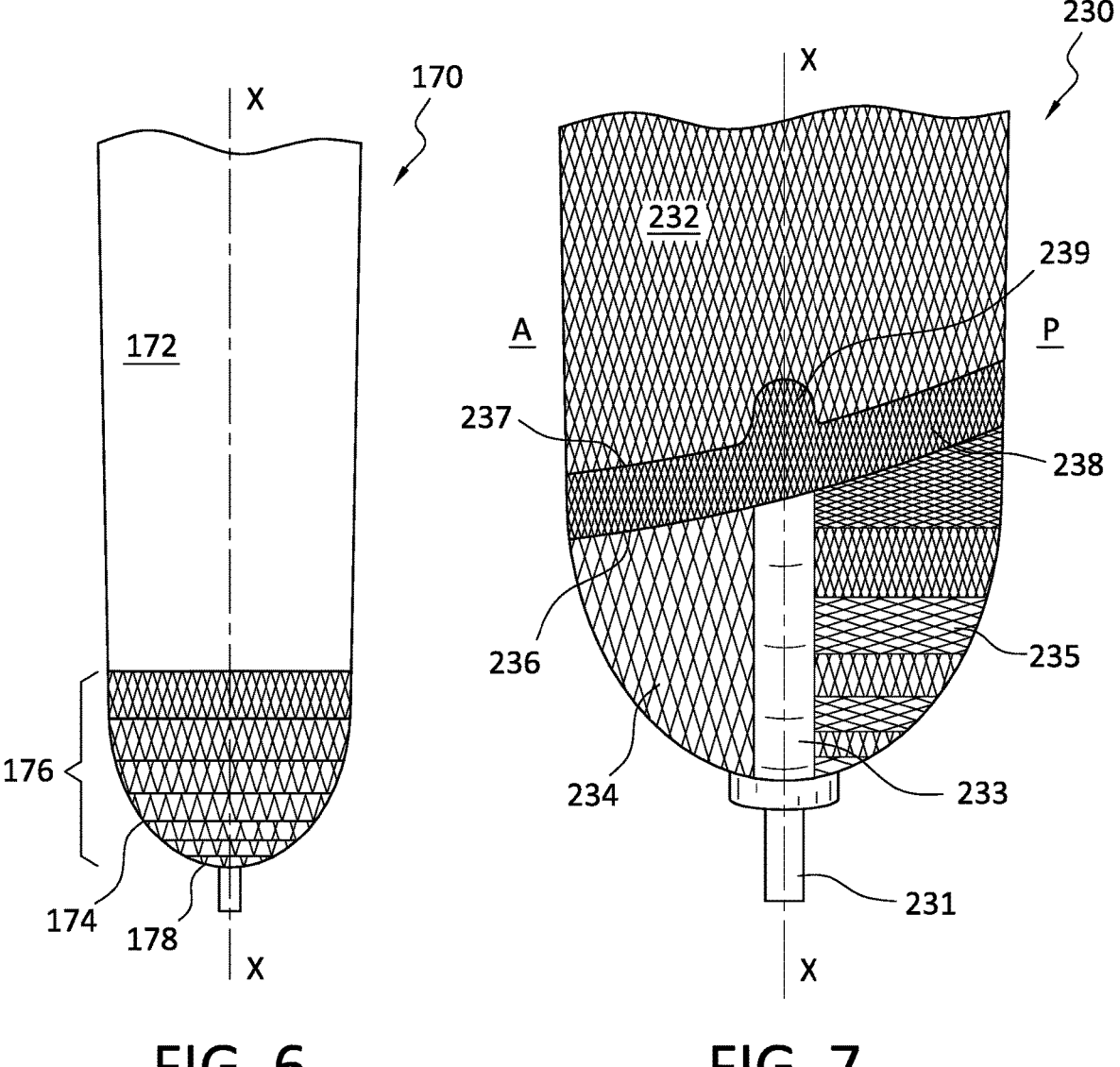
FIG. 6 is an elevational view showing of a variation of the liner of FIG. 1 having a gradient of axial elongation.
FIG. 7 is an elevational view showing a variation of the liner of FIG. 1 having features drawn from FIGS. 4A-6.

FIG. 6 exemplifies a liner 170 having a textile cover 172 with a distal portion 174 having a variably stretched gradient 176. For example, the distal end 178 may have a highest stretched point of the textile cover 172, and the distal portion 174 is stretched less towards or approaching a proximal end of the liner 170, and adjacent to a remainder of the textile cover 172 that is proximal the distal portion 174 and in a non-stretched configuration, as in foregoing embodiments.

FIG. 7 exemplifies a liner 230 having features of the aforementioned embodiments. The liner 230 has a textile cover 232 which may have an unstretched configuration such that it is generally unaltered from a natural state and corresponding properties. The liner 230 has a first distal end region 234 and a second distal end region 235, corresponding to anterior and posterior sides A, P, respectively, of the liner 230 and proximate a distal pin 231. The first and second distal end regions 234, 235 may have different elongation relative to one another and likewise from the textile cover 232. At least one elongate region 233 may divide the first and second distal end regions 234, 235 and may possess a different elongation from the textile cover 232, and/or the first and second distal end regions 234, 235.

An intermediate portion 238 may have first and second demarcations 236, 237 relative to the axis X-X, and may likewise have a different elongation from the first and second distal end regions 234, 235, and/or the at least one elongate region 233, and/or the textile cover 232. The intermediate portion 238 may have an elongate region 239 unto itself which may correspond to the at least one elongate region 233 or be individually disposed relative to the at least one elongate region 233. Any of the regions may have generally uniform elongation properties or may have variable properties. The regions may be prestretched and/or form a matrix separably formed and attached to the textile cover.

It is to be understood that not necessarily all objects or advantages may be achieved under any embodiment of the disclosure. Those skilled in the art will recognize that the liner may be embodied or carried out in a manner that achieves or optimizes one advantage or group of advantages as taught herein without necessarily achieving other objects or advantages as may be taught or suggested herein.

The skilled artisan will recognize the interchangeability of various disclosed features. Besides the variations described herein, other known equivalents for each feature can be mixed and matched by one of ordinary skill in this art to construct a liner in accordance with principles of the present disclosure. It will be understood by the skilled artisan that the features described herein may be adapted to other types of devices. Hence this disclosure and the embodiments and variations thereof are not limited to liners for prosthetic devices but can be utilized in any devices.

Although this disclosure describes certain exemplary embodiments and examples of a liner, it will be understood by those skilled in the art that the present disclosure extends beyond the specifically disclosed embodiments to other alternative embodiments and/or uses of the disclosure and obvious modifications and equivalents thereof. It is intended that the present disclosure should not be limited by the disclosed embodiments described above and may be extended to other applications that may employ the features described herein.

The invention claimed is:

1. A prosthetic liner having a central, longitudinal axis, comprising:
   a textile cover having at least first and second regions with textile configurations having first and second elongation properties, respectively, different from one another as defined relative to the central, longitudinal axis of the prosthetic liner;
   a layer of cured elastomeric material is located along an inner surface of the textile cover across the first and second regions;
   wherein the first and second regions are adjacent to one another along the central, longitudinal axis such that the second region is located proximally relative to the first region, the first and second regions extending circumferentially about the prosthetic liner;
   wherein the first region is in a prestretched configuration in at least one orientation relative to the central, longitudinal axis of the prosthetic liner, and locked and maintained in the prestretched configuration by the layer of cured elastomeric material,
   wherein the second region is in an unstretched configuration relative to the prestretched configuration first region with the layer of elastomeric material secured thereon;
   wherein the second elongation properties of the second region have greater axial elongation relative to the first elongation properties of the first region;
   wherein the first elongation properties have an elongation gradient in which elongation varies across the first region.

2. The prosthetic liner of claim 1, wherein the first region has a non-uniform shape as extending toward the second region.

3. The prosthetic liner of claim 1, wherein the first and second regions consist of a same textile cover continuously extending along a combined length of the first and second regions along the central, longitudinal axis in both circumferential and axial directions of the prosthetic liner.

4. The prosthetic liner of claim 1, wherein the textile cover forms an exterior of the prosthetic liner, and the layer of elastomeric material is located along an entirety of the textile cover extending continuously between the first and second regions.

5. The prosthetic liner of claim 1, wherein a demarcation is located between the first and second regions.

6. The prosthetic liner of claim 5, wherein the demarcation is transverse relative to the central, longitudinal axis of the prosthetic liner.

7. The prosthetic liner of claim 5, wherein the demarcation varies relative to the central, longitudinal axis of the prosthetic liner.

8. The prosthetic liner of claim 1, wherein the same elongation comprises radial and axial directions.

9. The prosthetic liner of claim 1, wherein the prosthetic liner has a closed-ended distal end and the first region comprising the closed-ended distal end of the prosthetic liner.

10. The prosthetic liner of claim 1, wherein the prosthetic liner has an open-ended proximal end and the second region comprising the open-ended proximal end of the prosthetic liner.

11. The prosthetic liner of claim 1, further comprising a distal end cap and a distal pin extending therefrom, the distal end cap being located over the first region.

12. The prosthetic liner of claim 1, wherein the first region is located in a distal portion of the prosthetic liner and the second region is located proximally relative to the first region from a demarcation of the first and second regions.

13. The prosthetic liner of claim 1, wherein the cured elastomeric material is a thermoplastic.

14. The prosthetic liner of claim 1, wherein the second region extending longer along the central, longitudinal axis than the first region such that first region is generally confined to the distal portion of the prosthetic liner.

\* \* \* \* \*